US006861498B1

(12) United States Patent
Imperante

(10) Patent No.: US 6,861,498 B1
(45) Date of Patent: Mar. 1, 2005

(54) GLYCERYL CITRATE POLYESTERS IN PERSONAL CARE

(75) Inventor: John Imperante, Somerville, NJ (US)

(73) Assignee: Phoenix Research Corporation, Somerville, NJ (US)

( * ) Notice: Subject to any disclaimer, the term of this patent is extended or adjusted under 35 U.S.C. 154(b) by 0 days.

(21) Appl. No.: 10/348,885

(22) Filed: Jan. 23, 2003

(51) Int. Cl.$^7$ .............................................. C08G 65/02
(52) U.S. Cl. ....................... 528/361; 528/272; 528/283; 528/300

(58) Field of Search ................................. 528/272, 283, 528/300, 361

(56) References Cited

U.S. PATENT DOCUMENTS 4,868,236 A    9/1989    O'Lenick, Jr.

*Primary Examiner*—Samuel A. Acquah

(57) ABSTRACT

The present invention relates to specific glyceryl alkoxylated citrate esters and their use in lipsticks. These polymers not only do not have a mal taste, but also have a very pleasant taste. This coupled with their use to prevent syneresis in lipsticks, make these products very desirable in lipstick applications.

10 Claims, No Drawings

GLYCERYL CITRATE POLYESTERS IN PERSONAL CARE

FIELD OF THE INVENTION

The present invention relates to specific glyceryl alkoxylated citrate esters and their use in lipsticks. These polymers not only do not have a mal taste, but also have a very pleasant taste. This coupled with their use to prevent syneresis in lipsticks, make these products very desirable in lipstick applications.

BACKGROUND OF THE INVENTION

The use of color cosmetics dates back to the times of the Egyptians. The adornment of the skin and more particularly, the lips with color has been important to humans for many centuries. A particular difficulty that is encountered with the use of pigmented products on the lips is the fact that the lips are in intimate contact with the tongue and taste is a major consideration as to weather a particular product is used on the lips.

Lipsticks are made up of a variety of materials that are combined to make the delivery of color to the lips. The formulations contain waxes, silicone resin, organic esters, pigments and other additives. The difference in solubility of these materials cause a problem called syneresis, a "bleeding" of a liquid phase from the wax phase. Additives like esters are used to minimize the occurrence of syneresis.

Unfortunately, since organic esters are made at elevated temperatures of compounds that have a tendency to oxidize, producing aldehydic and ketonic bodies that condense can contribute bad taste to these compounds.

THE INVENTION

Objective of the Invention

The present invention provides for a series of polyesters useful in the preparation of lipstick. The product has a very pleasant tart taste and can be used to overcome the mal taste of other lipstick ingredients.

Another aspect of the preset invention is lipstick formulations using the compounds of the present invention.

Other objectives will become apparent as the specification is read and understood.

SUMMARY OF THE INVENTION

The present invention is drawn to a series of novel polyesters made by the esterification reaction of glycerin or alkoxylated glycerin with citric acid. The resulting polyester is polar enough to minimize syneresis in lipsticks, provide humectancy to the lips due to the presence of the glycerin groups and most importantly provides a pleasant tart taste when applied to the lips.

DETAILED DESCRIPTION OF THE INVENTION

The present invention is drawn to a polyester made by the esterification reaction of citric acid which conforms to the following structure;

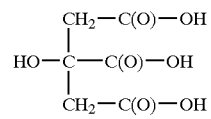

with an alkoxylated glycerin which conforms to the following structure;

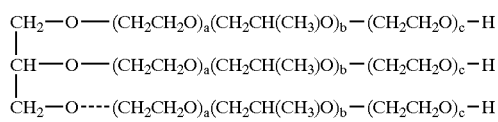

wherein;

a, b and c are each independently integers ranging from 0 to 20.

Preferred Embodiment

In a preferred embodiment, said esterification reaction is conducted at a temperature of between 150 and 220° C. in the presence of an insoluble tin catalyst, which is removed in a subsequent filtration step.

In another preferred embodiment, said the mole ratio of glycerin to citric acid ranges from 3:1 to 1:3.

In still another preferred embodiment, the mole ratio of glycerin to citric acid is 1:1.

In another preferred embodiment, a, b and c are each 0.

In another preferred embodiment, a and c are each 0, b is an integer ranging from 1 to 20. The propoxylated product has improved oil solubility over the combination ethoxylated/propoxylated or simply ethoxylated product.

In another preferred embodiment, a is 0, b and c are each integers ranging from 1 to 20. This product has outstanding liquidity over the other variations.

EXAMPLES

Citric Acid

Citric Acid is a natural product and an item of commerce available from a variety of sources, most notable Pfizer, and conforms to the following structure;

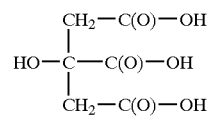

Examples 1–10 Alkoxylated Glycerin

Alkoxylated glycerin is an item of commerce available from Siltech Corporation Toronto Ontario Canada.

| Example | a | b | c |
|---|---|---|---|
| 1 | 0 | 0 | 0 |
| 2 | 0 | 5 | 0 |
| 3 | 0 | 10 | 10 |
| 4 | 5 | 5 | 5 |
| 5 | 20 | 20 | 20 |
| 6 | 10 | 10 | 10 |

-continued

| Example | a | b | c |
|---------|----|----|----|
| 7 | 2 | 10 | 2 |
| 8 | 10 | 2 | 10 |
| 9 | 0 | 20 | 0 |
| 10 | 20 | 0 | 20 |

Examples 10–20 Polyester
General Procedure

To the 60 grams of citric acid is added the specified amount of the specified glycerin alkoxylates (example 1–10) and 0.1% by weight of tin oxylate catalyst. The reaction is a mixture of liquid alkoxylates and solid citric acid. The reaction mass is heated to between 170 and 180° C., and held for eight hours. During this time the solid cirtric acid reacts with the glycerin alkoxylates, becomes clear and homogeneous. The product is used without additional purification.

| | | Alkoxylated Glycerin |
|---|---|---|
| Example | Grams | Example |
| 11 | 30.0 | 1 |
| 12 | 250.0 | 2 |
| 13 | 540.0 | 3 |
| 14 | 765.0 | 4 |
| 15 | 2970.0 | 5 |
| 16 | 1500.0 | 6 |
| 17 | 796.0 | 7 |
| 18 | 1028.0 | 8 |
| 19 | 1270.0 | 9 |
| 20 | 1790.0 | 10 |
| 21 | 10.0 | 1 |
| 22 | 83.3. | 2 |
| 23 | 180.0 | 3 |
| 24 | 255.0 | 4 |
| 25 | 990.0 | 5 |
| 26 | 500.0 | 6 |
| 27 | 796.0 | 7 |
| 28 | 343.0 | 8 |
| 29 | 423.0 | 9 |
| 30 | 596.0 | 10 |
| 31 | 90.0 | 1 |
| 32 | 750.0 | 2 |
| 33 | 1620.0 | 3 |
| 34 | 2295.0 | 4 |
| 35 | 8910.0 | 5 |
| 36 | 4500.0 | 6 |
| 37 | 2388.0 | 7 |
| 38 | 3084.0 | 8 |
| 39 | 3810.0 | 9 |
| 40 | 5370.0 | 10 |

Applications

The compounds of the present invention are capable of being prepared having a variety of different desirable and surprising attributes. Polarity, water solubility, oil solubility and silicone solubility.

Compounds in which a+c is equal to or greater than 7 are doing to be water-soluble. Compounds in which a+c is between 5 and 7 will be water dispersible. If a+c is less than 5 the molecule will be insoluble in water.

Compounds in which b is 0, are solids, or very thick immobile liquids. Compounds in which b is 3 or greater are liquids. Compounds in which b is above 12 have improved dispersibility in oil.

Compounds in which b is greater than or equal to 3, and a+c is equal to or greater than 7 are water-soluble liquids.

All compounds have the desire tart taste, which allow them to be used to mask any mal taste that exists in lipstick formulation ingredients. This allows the formulator wider latitude of compounds used in their formulations.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A polyester made by the esterification reaction of citric acid which conforms to the following structure;

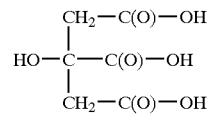

with an alkoxylated glycerin which conforms to the following structure;

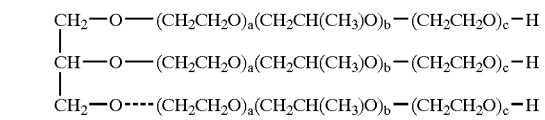

wherein;

a, b and c are each independently integers ranging from 0 to 20.

2. A polyester of claim 1 wherein said esterification reaction is conducted at a temperature of between 150 and 220° C. in the presence of a tin catalyst.

3. A polyester of claim 1 wherein the mole ratio of glycerin to citric acid ranges from 3:1 to 1:3.

4. A polyester of claim 1 wherein the mole ratio of glycerin to citric acid is 1:1.

5. A polyester of claim 1 wherein a, b and c are each 0.

6. A polyester of claim 1 wherein a and c are each 0, b is an integer ranging from 1 to 20.

7. A polyester of claim 2 wherein the mole ratio of glycerin to citric acid ranges from 3:1 to 1:3.

8. A polyester of claim 2 wherein the mole ratio of glycerin to citric acid is 1:1.

9. A polyester of claim 2 wherein a, b and c are each 0.

10. A polyester of claim 2 wherein a and c are each 0, b is an integer ranging from 1 to 2.

* * * * *